(12) United States Patent
Schootstra et al.

(10) Patent No.: US 12,083,323 B2
(45) Date of Patent: Sep. 10, 2024

(54) NEEDLE HUB AND SYRINGE ARRANGEMENT

(71) Applicant: SJJ SOLUTIONS B.V., Delft (NL)

(72) Inventors: Sander Schootstra, Delft (NL); Joost Schootstra, Delft (NL); Jasper Schootstra, Delft (NL)

(73) Assignee: SJJ Solutions, B.V., Delft (NL)

( * ) Notice: Subject to any disclaimer, the term of this patent is extended or adjusted under 35 U.S.C. 154(b) by 546 days.

(21) Appl. No.: 17/259,527

(22) PCT Filed: Jul. 10, 2019

(86) PCT No.: PCT/NL2019/050430
§ 371 (c)(1),
(2) Date: Jan. 11, 2021

(87) PCT Pub. No.: WO2020/013692
PCT Pub. Date: Jan. 16, 2020

(65) Prior Publication Data
US 2021/0178078 A1 Jun. 17, 2021

(30) Foreign Application Priority Data
Jul. 12, 2018 (NL) .................................. 2021294

(51) Int. Cl.
*A61M 5/315* (2006.01)
*A61M 5/32* (2006.01)
*A61M 5/34* (2006.01)

(52) U.S. Cl.
CPC ...... *A61M 5/31511* (2013.01); *A61M 5/3293* (2013.01); *A61M 5/347* (2013.01); *A61M 2005/31516* (2013.01)

(58) Field of Classification Search
CPC ............ A61M 5/31511; A61M 5/3293; A61M 5/347; A61M 2005/31516
See application file for complete search history.

(56) References Cited

U.S. PATENT DOCUMENTS

| 3,096,763 | A | 7/1963 | Mcconnaughey |
| 3,306,291 | A | 2/1967 | Burke |
| (Continued) | | | |

FOREIGN PATENT DOCUMENTS

| CN | 2880125 | 3/2007 |
| CN | 102028992 | 4/2011 |
| (Continued) | | |

OTHER PUBLICATIONS

International Search Report, issued in PCT/NL2019/050430, mailed Oct. 24, 2019.

(Continued)

*Primary Examiner* — Bradley J Osinski
(74) *Attorney, Agent, or Firm* — Ferguson Case Orr Paterson LLP

(57) ABSTRACT

The total volume of fluid in a syringe may not be equal to the total volume of fluid that can be pressed out of the syringe: a dead volume may be left in an arrangement of the syringe and a needle hub provided with the syringe. To reduce the dead volume, a needle hub and syringe arrangement is provided which are shaped complementary to each other. More specifically, a shape of an end-plane of a piston comprised by the syringe is complementary to a shape of a plane in which an opening of a cannula bore of the needle hub is provided. The shapes are such that the volume inside the syringe once occupied by the fluid may be occupied by the piston after fully pressing down on the piston, or only a substantially small volume of fluid may be left between the cannula opening and the syringe.

15 Claims, 3 Drawing Sheets

(56) References Cited

U.S. PATENT DOCUMENTS

| | | | |
|---|---|---|---|
| 3,491,128 A | 1/1970 | Dewhurst | |
| 4,040,421 A | 8/1977 | Young | |
| 4,240,425 A | 12/1980 | Akhavi | |
| 4,720,285 A | 1/1988 | Pickhard | |
| 5,069,670 A | 12/1991 | Vetter | |
| 2004/0102740 A1 | 5/2004 | Meloul | |
| 2008/0262435 A1 | 10/2008 | Erickson | |
| 2015/0157811 A1* | 6/2015 | Zuidema | A61M 5/34 285/8 |
| 2016/0008545 A1* | 1/2016 | Brothers | A61M 5/3134 604/222 |

FOREIGN PATENT DOCUMENTS

| | | |
|---|---|---|
| CO | 6531493 | 9/2012 |
| EP | 0144483 | 6/1985 |
| JP | 2005525836 | 9/2005 |
| JP | 2010504106 | 2/2010 |
| JP | 2016508853 | 3/2016 |
| JP | 2016539765 | 12/2016 |
| TW | 201113060 | 4/2011 |
| WO | 03018091 | 3/2003 |
| WO | 2007131086 | 11/2007 |
| WO | 2009102624 | 8/2009 |
| WO | 2011040222 | 4/2011 |
| WO | 2011056214 | 5/2011 |
| WO | 2014011046 | 1/2014 |

OTHER PUBLICATIONS

Written Opinion, issued in PCT/NL2019/050430, mailed Oct. 24, 2019.

Notice of Refusal issued in Japanese Application No. 2021-523543 drafted Mar. 28, 2023.

* cited by examiner

NEEDLE HUB AND SYRINGE ARRANGEMENT

TECHNICAL FIELD

The present invention relates to the field of a needle hub and syringe arrangement.

BACKGROUND

Fluids, such as liquid medicine, are often provided in a syringe and needle hub arrangement for providing a predetermined amount of the fluid to for example a body part of a patient using a needle. Worldwide, a lot of liquid medicine is discarded without being used as it is left after use in a syringe in what is known as a dead volume. Conventional needle hubs which are arranged to be provided on syringes are often designed to a specific standard, such as an ISO standard, and are arranged to fit on a plurality of different syringes. Therefore, a perfect fit will not be achieved and a dead volume will be present between syringe and needle hub.

WO2014011046 discloses a needle and syringe arrangement with a frustoconical male slip fitting and a frustoconical female slip fitting. The male slip fitting is insertable into the female slip fitting establishing a press fitted connection with a small dead volume. In this needle and syringe arrangement, the barrel may be inserted into the needle. When the piston has been pressed against the needle hub, and the maximum amount of fluid has been pressed out of the arrangement, a part of the piston protrudes from the barrel. This protrusion creates a dead volume between the barrel, the piston, and the needle hub.

US20160008545A1 discloses a low-waste needle and syringe assembly for injecting a fluid into a patient. syringe. A syringe tip defining a substantially frusto-conical interior void extends from an end wall of the syringe frusto-conical member of the needle hub matingly engages the frusto-conical void of the syringe tip when the hub is secured to the syringe, forming a fluid-tight seal. A plunger positioned in the fluid chamber can be depressed by a user, and a piston cap attached to the plunger urges fluid in the chamber out of the chamber through the syringe tip and into the needle. The piston cap matingly engages the end wall of the syringe so that substantially all fluid is urged from the chamber to the needle.

SUMMARY

In the needle and syringe arrangement of WO2014011046, the barrel end plane is bevelled, and the abutment plane of the needle hub against which the piston is to abut is tapered towards the cannula opening. Furthermore, only a small part of the surface of the plunger end may actually contact the abutment plant of the needle hub. As such, a relatively large volume of fluid may be trapped between the plunger, barrel and needle hub. This trapped volume forms part of the residual dead volume. As a result hereof, the residual dead volume of this needle and syringe arrangement may not be zero, or even close to zero.

In the needle and syringe assembly of US20160008545A1, the cannula opening extends into the barrel of the syringe when the needle hub is placed over the proximal end of the barrel. Furthermore, when the piston is in the second position, and thus the dead volume is minimized, the piston does not abut the plane surrounding the cannula opening, or only a small area of the piston end plane abuts the plane surrounding the cannula opening. As a result hereof, the residual dead volume of this needle and syringe assembly may not be zero, or even close to zero.

The aim of the present invention is to further reduce the dead volume in a needle hub and syringe arrangement. Such a dead volume may be defined as the volume of fluid inside the syringe which cannot be pressed out of the syringe and needle hub arrangement using a piston of the syringe. The dead volume will thus remain in the arrangement after use of the arrangement. However, when using the term dead volume in the following description, only the dead volume due to a mismatch in shape of the syringe and the needle hub is implied. Reducing the dead volume in the cannula bore of the needle hub will not be considered.

A first aspect provides a needle hub and syringe arrangement, comprising a needle hub and a syringe comprising a barrel and a piston. The needle hub comprises an axially oriented cannula bore comprising a cannula opening, wherein the cannula opening is surrounded by an abutment plane. The barrel comprises an axially elongated hollow cylinder. A first of the needle hub and the barrel is arranged as a male part arranged to be received by a second of the needle hub and the barrel arranged as a female part. The piston comprises at a proximal end an end-plane shaped complementary to at least part of the abutment plane, and the piston is arranged to be translated axially within the barrel between a first position and a second position. In the first position, a volume arranged for holding a fluid is defined by part of an inner wall of the barrel, the end-plane of the piston, and at least part of the abutment plane.

In the second position, the end-plane of the piston abuts the abutment plane and the fluid volume left in the arrangement is reduced to the dead volume. This dead volume may be defined by part of an inner wall of the barrel, the end-plane of the piston, and at least part of the abutment plane. Alternatively, it may be defined by the end-plane of the piston, and at least part of the abutment plane—such may be in particular the case if there is a mismatch in some way between the end-plane of the piston, and at least part of the abutment plane, for example due to manufacturing issues.

The needle hub and syringe arrangement is typically used as follows: the needle hub and syringe are press-fitted together such that a watertight seal is provided between the needle hub and syringe. Preferably, a distal end of the syringe, at which the end-plane of the piston is located in the second position, abuts to the abutment plane.

A needle may be provided to the needle hub, and a fluid is sucked into the barrel of the syringe through a cannula bore of the needle hub by moving the piston inside the barrel away from the needle hub, creating a low pressure inside the barrel towards which a fluid will flow. Using volume indicators for example provided on the outside of a transparent barrel, the user may suck up a desired volume of fluid. Next, the user will press the piston back again towards the needle hub until a small drop emerges from the needle or the cannula bore of the needle hub. The drop will indicate to the user that the dead volume has been totally filled with the fluid and that the needle hub and syringe arrangement is ready for use.

In an alternative use of the needle hub and syringe arrangement, first a filter needle is fitted on the syringe. Fluid is sucked into the barrel through the filter needle, wherein the filter needle is arranged to filter out possible contaminants which might be present in the fluid and are undesired. Filter needles often comprise a larger diameter needle, wherein the larger diameter reduces the risk of unwanted air bubbles being sucked into the barrel. Furthermore, filter needles may comprise a longer needle which may reach the bottom of an ampule out of which the fluid will be sucked. After the fluid has been sucked into the syringe, the filter needle may be removed and the needle hub may be press-fitted on the barrel.

Different complementary shapes of the barrel and the piston next to being cylindrical are envisioned as well. Any hollow barrel shape and corresponding piston shape that will fit into the hollow barrel may be used in the arrangement.

The complementary shapes of the end-plane of the piston and the abutment plane provide that a small or even absent residual volume is left between the barrel and the needle when the piston has been moved to the second position.

Typically, the arrangement according to the present invention may reduce wasted fluid by 0.05 mL compared to conventional syringe and needle hub arrangement. Considering the costs of medical fluids and the amount of syringe and needle hub arrangement used worldwide the invention presents a considerable advantage over the arrangements known in the art.

It is noted that with the wording "piston" actually pistons as well as plungers are meant or any other body performing such function in the barrel of the syringe.

In an embodiment of the arrangement, the end-plane of the piston and the abutment plane are substantially planar and/or parallel. In such embodiments, it may be at least partially prevented that fluid is trapped between the piston and the barrel and cannot leave the arrangement. As such, dead volume or residual volume may be reduced or preferably even prevented.

In embodiments of the arrangement, when the piston is in the second position, the end-plane of the piston, the abutment plane and the cannula opening are substantially parallel and aligned. In such embodiments, it may be at least partially prevented that fluid is trapped between the piston and the barrel and cannot leave the arrangement. As such, dead volume or residual volume may be reduced or preferably even prevented.

In an embodiment of the arrangement, the volume constrained between the end-plane of the piston, the abutment plane and a part of the inner wall of the barrel is smaller than 0.005 mL and preferably zero.

In a preferred embodiment of the arrangement, the abutment plane comprised by the needle hub is oriented substantially perpendicular to the axial direction. The complementary shape of the end-plane of the piston is also oriented substantially perpendicular to the axial direction. When both shapes are flat, the embodiment has the advantage that the syringe and needle hub may be arranged regardless of the angular orientation of barrel relative to the needle hub.

The needle hub may comprise a second opening opposite to the cannula opening for receiving a needle.

In a further preferred embodiment of the arrangement, the needle hub is arranged as the female part and the needle hub comprises a cavity for receiving at least part of or with provided therein at least part of the barrel arranged as the male part such that part of an outer wall of the barrel is press-fitted against at least part of an inner wall of the cavity of the needle hub.

In such an embodiment, an inner wall of the cavity of the needle hub may comprise one or more recesses wherein at the one or more recesses the outer wall of the barrel when the barrel is inserted into the cavity does not touch the inner wall of the cavity. The recesses decrease the contact surface between the cavity and the outer wall allowing an easier insertion of the barrel into the cavity.

In embodiments of the arrangement, the needle hub does not extend into the syringe. For example, when the needle hub is the female part and the barrel is the male part, the barrel extends into the needle hub but no part of the needle hub protrudes into the barrel. Hence, the volume available for fluid in the barrel is not decrease due to any part of the needle hub protruding into the barrel. For providing the fit between the barrel and the needle hub, some part of the needle hub may extend outside the barrel, and for example engage an outer surface of the barrel or any structure provided at the outer surface of the barrel. This may for example result in a higher accuracy of fluid volume that is to be dispensed from the arrangement.

To provide a better lock between the syringe and the needle hub than just friction between the two parts, a first of the outer wall of the barrel and the inner wall of the cavity may comprise a protruding section and a second of the outer wall of the barrel and the inner wall of the cavity may comprise a receding section corresponding to the protruding section such that when the barrel is inserted into the cavity the protruding section may engage with the receding section forming a locking engagement.

In embodiments of the arrangement, the barrel end-plane may constitute the furthest point of the syringe reaching towards the needle hub. In such embodiments, and optionally also in other embodiments, the cannula opening does not reach within the syringe. In other words, at the proximal end of syringe, the syringe does not extend beyond the abutment plane of the needle hub. In such embodiments, a residual volume is the piston is in the second position may be decreased up to a zero volume, next to other embodiments in which this may be possible.

In embodiments of the arrangement, when the piston is in the second position, at least 20%, preferably at least 30%, even more preferably at least 40% or at least 50%, and even more preferably at least 60%, at least 70%, at least 80% or even more preferably at least 90% of the surface area of the piston end-plane contacts the abutment plane. As such, the volume of fluid that may be trapped between the piston and the barrel, which residual volume cannot be pressed out of the syringe, may be reduced to a volume smaller than 0.005 mL or even to zero.

A second aspect provides a needle hub, comprising a cavity arranged for receiving a barrel, an axially oriented cannula bore comprising a cannula opening. The cannula opening is in fluid connection with the cavity, and the cannula opening is surrounded by a substantially flat abutment plane. Further more, the abutment plane is oriented substantially perpendicular to the axial direction. The orientation allows the piston to align with a substantially flat end-plane of a piston which is also oriented substantially perpendicular to the axials direction.

The needle hub may be used in arrangements with syringes other than the syringes that will be discussed here. Any syringe which is compliance with ISO 594-1 may be used in an arrangement in the needle hub. Although in such arrangements the dead volume is not reduced as much as with the arrangement according to the present invention, still a reduction in dead volume may be achieved due to the substantially perpendicular to the axial direction oriented abutment plane.

A third aspect provides a syringe, comprising a barrel, comprising an axially elongated hollow cylinder, arranged to at least partly be inserted into a cavity of a needle hub. The syringe further comprises an axially elongated piston, arranged to be translated axially within the barrel. The piston comprises a substantially flat end-plane oriented substantially perpendicular to the axial direction.

BRIEF DESCRIPTION OF THE DRAWINGS

The various aspects and embodiments thereof will now be discussed in conjunction with drawings. In the drawings.

DESCRIPTION OF THE EMBODIMENTS

Figure 1:
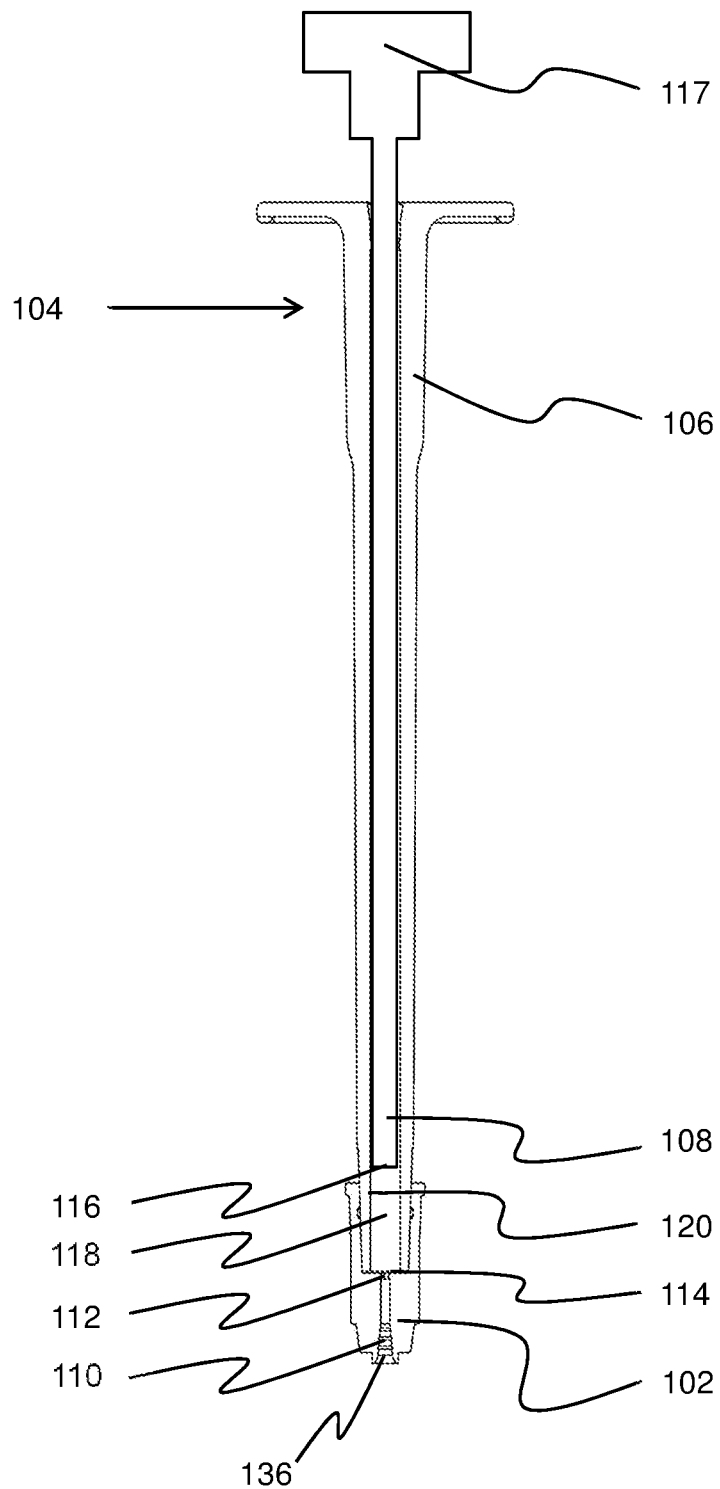
FIG. 1 shows a needle hub and syringe arrangement.

FIG. 1 shows an embodiment of a needle hub and syringe arrangement 100, comprising a needle hub 102 and a syringe 104 comprising a barrel 106 and a piston 108. The needle hub 102 comprises an axially oriented cannula bore 110 comprising a cannula opening 112, which is surrounded by an abutment plane 114. The barrel 106 comprises an axially elongated hollow cylinder.

In the arrangement 100, a first of the needle hub 102 and the barrel 106 is arranged as a male part arranged to be received by a second of the needle hub 102 and the barrel 106 arranged as a female part. In the embodiment as shown in FIG. 1, the needle hub 102 is arranged as the female part arranged to receive the barrel 106 as the male part.

The piston 108 comprises an end-plane 116 at a proximal end, which is shaped complementary to the abutment plane 114 of the needle hub 102. The piston 108 is arranged to be translated axially within the barrel 106 between a first position and a second position. In the first position, a fill volume 118 arranged for holding a fluid is defined by part of an inner wall 120 of the barrel, the end-plane 116 of the piston, and at least part of the abutment plane 114. In the second position, the fill volume 118 is reduced to zero and only the dead volume is left in the arrangement 100 because in the second position the end-plane 116 of the piston abuts the abutment plane 114.

On a distal end of the piston 108, opposite to the end-plane 116, the piston may be provided with a handle 117 arranged for allowing easy control of the axial position of the piston 108 inside the barrel 106 to a user.

By translating the piston 108 within the barrel 106 from the second position to the first position, a fluid may be sucked into the volume 118 through the cannula opening 112. With the opposite movement from the first position to the second position, the fluid present in the volume 118 may be ejected out of the volume 118 through the cannula opening 112.

When the syringe is provided 104 without the needle hub 102, the barrel 106 itself may be placed in contact with a fluid that is to be sucked into the barrel 106, and by moving the piston 108 inside the barrel 106 the fluid may be sucked into the barrel 106. Alternatively, another needle like a filter needle arrangement may be used. After a desired amount of fluid is present in the barrel 106, the needle hub 102 may be provided to the syringe 104 to form the arrangement 100.

In an embodiment of the needle hub 102, the needle hub 102 comprises a second opening 136 opposite to the cannula opening 112 for receiving a needle. The cannula bore 110 may be tapered away from the cannula opening 112 such that the needle may be inserted more easily. After the needle has been inserted, it may be glued to the cannula bore 110. The second opening 136 may additionally or alternatively be arranged to be connected to another device arranged to receive or provide fluid respectively from or to the assembly 100, for example medical tubing, a bag or a catheter.

The shape of the end-plane 116 of the piston 108 is complementary to the shape of the abutment plane 114. Hence, the volume 118 constrained between the end-plane 116 of the piston 108, the abutment plane 114 and the part of the inner wall 120 of the barrel 106 between the end-plane 116 and the abutment plane 114 will be very small when the piston 108 is in the second position. Preferably, the volume 118 is smaller than 0.01 mL, even more preferably smaller than 0.005 mL when the piston 108 is in the second position.

In a preferred embodiment of the arrangement 100, the end-plane 116 of the piston 108 is a substantially flat surface provided perpendicular to the axial direction of the piston 108. The complementary shape of the abutment plane 114 to this embodiment of the piston 108 is a substantially flat shaped abutment plane 114 provided perpendicular to the axial direction of the needle hub 102.

Different complementary shapes of the end-plane 116 of the piston 108 and the abutment plane 114 are envisioned as well, for example a tapered end-plane 116 and a similarly tapered abutment plane 114, or a substantially flat end-plane provided at an angle relative to the axial direction of the piston 108, and a abutment plane 114 provided substantially flat at the same angle.

A further advantage of the small or even absent residual volume 118 may be an increase in accuracy of the amount of fluid inside the syringe 104 as the amount of fluid inside the syringe 104 substantially equals the volume 118. The volume of a dead volume is often unknown or only known to a certain degree of accuracy. Syringes such as the syringe 104 in the arrangement 100 of the present invention are often used for very small volumes of liquid, typically smaller than 1 mL, or even as small as 0.5 mL, or even more as small as 0.3 mL. With these small volumes, the dead volume is preferred to be as small as possible, especially small compared to the fluid volume that is to be ejected from the arrangement 100.

Because the sizes of the syringe may differ per application, the dead volume may also be specified as a percentage of the maximum fluid capacity of the barrel. For example, an embodiment of the barrel holds a maximum fluid volume of 0.3 mL. A preferred dead volume of less then 0.01 mL results in a dead volume percentage of 3.33%. Even more preferred is a dead volume percentage smaller than 3%, even more preferably a dead volume percentage smaller than 2%, and still even more preferably a dead volume percentage smaller than 1%.

Another cause of the dead volume may be manufacturing tolerances of the end-plane 116, the distal end of the barrel 106 and the abutment plane 114, which causes a mismatch in correspondence between said two planes. It is therefor preferred to manufacture the piston 108 and the needle hub 102 to a very high degree of manufacturing accuracy.

Figure 2A:
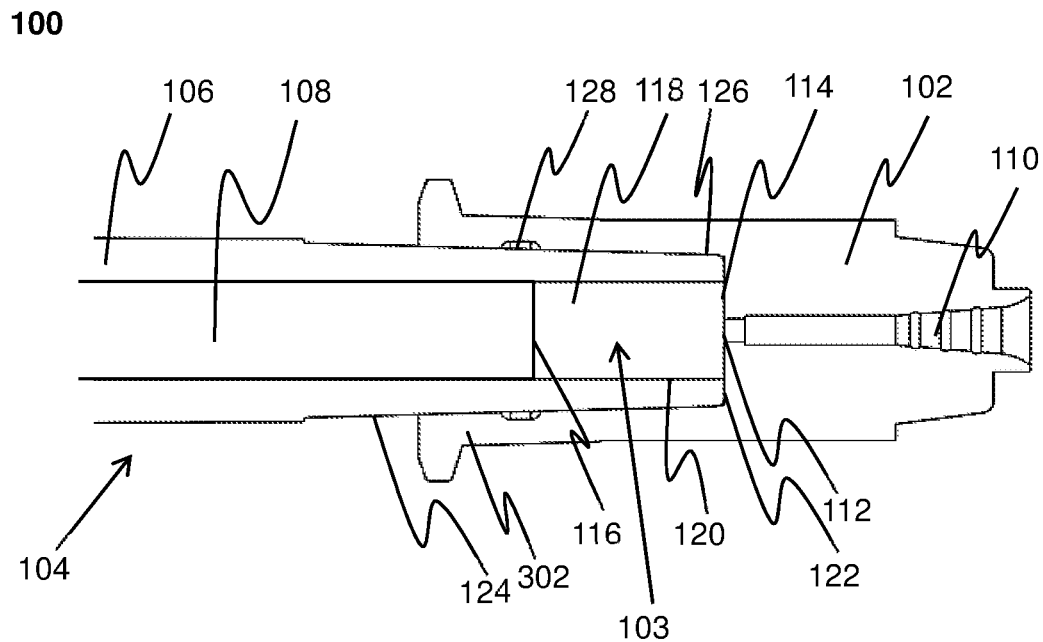
FIG. 2A shows a detailed view of a part of the arrangement.

In order to achieve such a high degree of manufacturing accuracy, the needle hub and the barrel may be injection moulded. As injection moulding still results in some inaccuracies, moulds may be used that provide a plurality of at least one of the needle hubs and barrels. A best match may then be searched between the plurality of combinations of needle hubs and barrels which results in the smaller dead volume FIG. 2A shows a detailed view of a part of the arrangement 100 comprising the needle hub 102 and syringe 104 comprising the barrel 106 and inserted into the barrel 106 and the piston 108. In the arrangement 100 as shown in FIG. 2A, the barrel 106 is arranged as the male part, which is arranged to be inserted in to a cavity 103 comprised by the needle hub 102 as the female part. The barrel 106 may be press-fitted into the cavity 103 of the needle hub 102 such that a watertight seal is provided between an outer surface 124 of the barrel 106 and an inner surface 126 of the cavity 103 of the needle hub 102.

The press-fit fitting of the barrel 106 into the cavity 103, a Luer-slip connection may be used. In such a case, the barrel 106 and the cavity 103 may be tapered according to, for example, the ISO 80369-7:2016 standards, or at an angle on approximately 6%.

Figure 3:
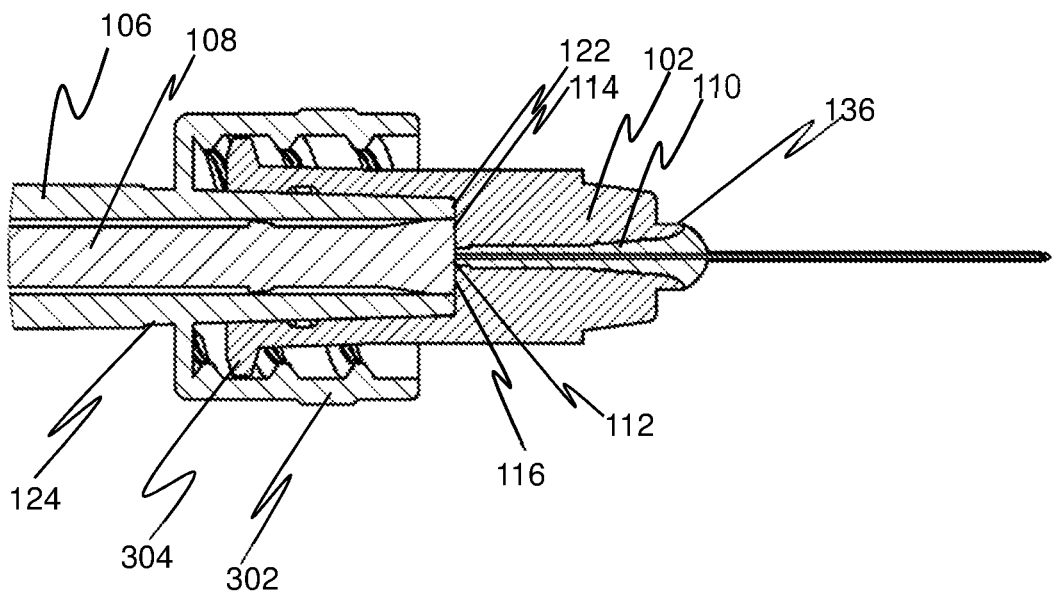
FIG. 3 shows another embodiment with a Luer Lock coupling.

Alternatively, a Luer-Lock connection as an example of a threaded connection between barrel 106 and needle hub 102 may be used, FIG. 3 shows part of an embodiment of the needle hub and syringe arrangement 100, wherein the barrel 106 is provided with a threaded section 302 arranged to receive the needle hub 102. The threaded section 302 may be designed according to the ISO 80369-7:2016 standard. The threaded section 302 in FIG. 3 is arranged as a skirt part protruding from the outer wall 124 of the barrel 106.

The needle hub 102 as shown in FIG. 3 is provided with a protrusion 304 as an example of a protrusion arranged to engage with the threaded section such that an axial connection may be achieved between the barrel 106 as a part of the syringe 104 and the needle hub 102. Alternatively, the protrusion 304 may be arranged as a thread, shaped complementary to the thread of the threaded section 302 of the barrel 106. For achieving the axial connection, the needle hub 102 may be screwed into the threaded part of the syringe 104.

The needle hub 102 as shown in FIG. 2A comprises a skirt part 302. The skirt part 302 surrounds the cavity 103, and may be arranged to engage the outer surface 124 of the barrel 106, for example to form a fluid-tight fit. The cannula opening 112 is not provided in the cavity 103, and is hence not surrounded by the skirt part 302. As such, when a needle is inserted into the cannula 110, the needle may not extend into the cavity 103. Then, when the barrel 106 is partially inserted at its proximal end into the cavity 103, the cannula opening 112 does not extend into the barrel 106, and a needle may also not extend into the barrel 106. This leaves all the inner volume of the barrel 106 at its proximal end available for fluid, which may contribute to the accuracy of fluid dosage.

The barrel 106 comprises a barrel end-plane 122, which, when the barrel 106 is inserted into the needle hub 102 may abut the abutment plane 114. In the second position of the piston, the barrel end-plane 122 and the end-plane 116 are preferably substantially at the same level, i.e. in the same plane. With such an abutment, a volume constrained between the barrel end-plane 122, the abutment plane 114, the piston 108 in the second position and, optionally, the inner wall of the barrel 106, is substantially negligible.

When the barrel end-plane 122 abuts the abutment plane 114, the cannula opening 112 does not extend within the barrel 106 or in the syringe 104. In the embodiment of FIG. 2A, the barrel end-plane 122 is the further extending point of the barrel 106 at the proximal end, and also of the syringe 104.

In another embodiment of the arrangement 100, when the barrel 106 is inserted into the needle 102, the barrel end-plane 120 does not abut the abutment plane 114 but is positioned at a small distance away from the abutment plane 114. In such an embodiment, a press-fit between the barrel 106 and the needle hub 102 is ensured as a maximum axial depth by which the barrel 106 may be inserted in the needle hub 102 is defined by the diameter of the inner surface 126 of the cavity 103 and the outer surface 124 of the barrel 108, as opposed to the abutting of the abutment plane 114 by the barrel end-plane 122.

As shown in FIG. 2A, the barrel 106, or at least one end thereof, may be embodied substantially as a tube, wherein the barrel end-plane 120 is a donut-shaped plane, with an inner radius and an outer radius.

Figure 2B:
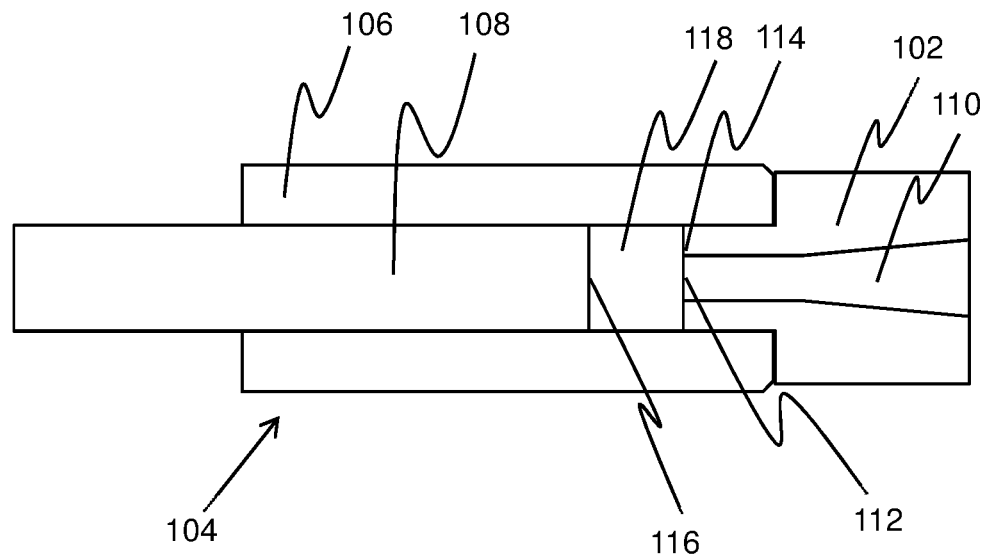
FIG. 2B shows a detailed view of a part of another embodiment of the arrangement.

FIG. 2B shows an embodiment of the arrangement 100 with the needle hub 102 as the male part partially inserted into the barrel 106 as the female part. In this embodiment, the needle hub 102 is press-fitted into the barrel 106, such that a watertight seal is provided between the needle hub 102 and the barrel 106 to prevent fluid and liquid in particular from leaking between the needle hub 102 and the barrel 106 when fluid is present in the volume 118, and especially when the piston 108 is moved towards the second position and fluid is pressed out of the volume 118 through the cannula bore 110.

Now returning to FIG. 2A, in an embodiment of the needle hub 102, the inner wall 126 of the cavity 103 comprises one or more recesses 128. The one or more recesses 128 are arranged such that when the barrel 106 is inserted into the cavity 103 a part of the outer wall of the barrel 124 does not touch the inner wall 126 of the cavity 103 at the one or more recesses 128. The recesses 128 are provided concentrically around an axis of the needle hub 102, passing through the cannula bore 110. These recesses allow for an easier insertion of the barrel 106 into the cavity 103.

Additionally or optionally, to further ease the insertion of the barrel 106 into the cavity 103, the cavity 103 may be tapered towards the cannula bore 110. An outer circumference 124 of the barrel 106 may also be tapered corresponding to the taper of the cavity 103.

Figure 2C:
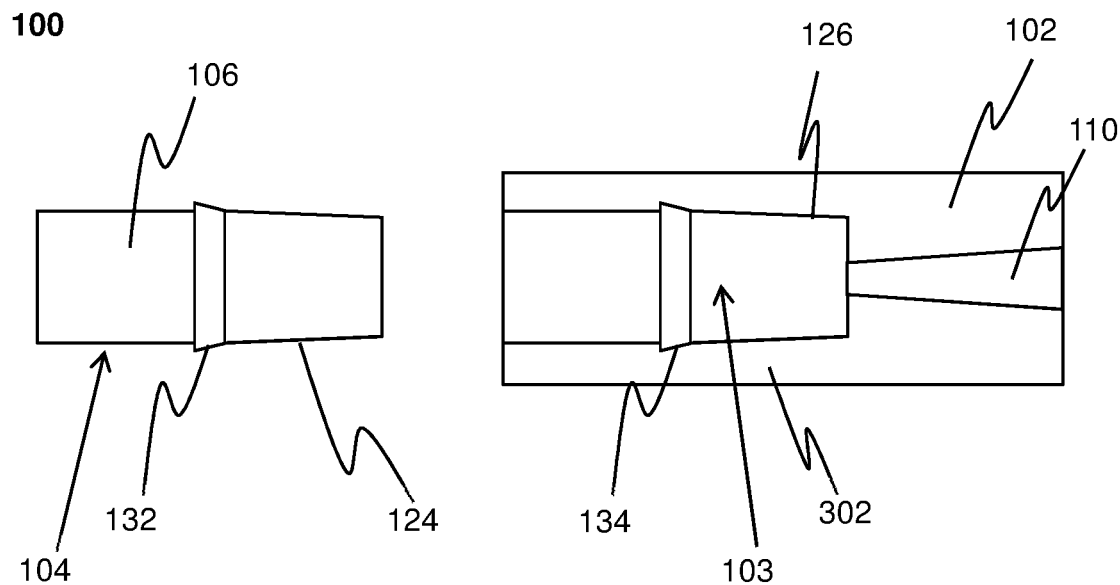
FIG. 2C shows an exploded view of a part of an embodiment of the arrangement.

FIG. 2C shows an exploded view of part of an embodiment of the arrangement 100 with the syringe 104 comprising the barrel 106, and the needle hub 102. In this embodiment, the inner wall 126 of the cavity 103 of the needle hub 102 comprises a receding section 134 corresponding to a protruding section 132 provided on the outer wall of the barrel 124. When the barrel 106 is inserted into the cavity 103, the protruding section 132 engages the receding section 134 and the barrel 106 is harder to remove again from the cavity 103. Preferably, the protruding section 132 and the receding section 134 are provided circumferentially. Furthermore, a plurality of at least one of the protruding sections and receding section may be provided to provide a plurality of points of engagement between the barrel 106 and the needle hub 102.

In another embodiment of the arrangement 100, the inner wall 126 of the cavity 103 comprises the protruding section and the outer wall of the barrel 124 comprises the protruding section.

In embodiments of the arrangement 100, a first of the barrel 106 and the cavity of the needle hub 103 comprises a resilient material with a stiffness lower than a stiffness of a second of the cavity of the needle hub 103 and the barrel 106. A stiffness of a material may be defined as the amount of force required to deform the material elastically and may be expressed for example in N/mm. Such a difference in stiffness between the male part and the female part allows either the outer circumference of the male part or the inner circumference of the female part to elastically deform when the male part is inserted into the female part. This elastic deformation may provide a watertight press-fit between the male part and the female part.

In summary, the total volume of fluid in a syringe may not be equal to the total volume of fluid that can be pressed out of the syringe: a dead volume may be left in an arrangement of the syringe and a needle hub provided with the syringe. To reduce the dead volume, a needle hub and syringe arrangement is provided which are shaped complementary to each other. More specifically, a shape of an end-plane of a piston comprised by the syringe is complementary to a shape of a plane in which an opening of a cannula bore of the needle hub is provided. The shapes are such that the volume inside the syringe once occupied by the fluid may be occupied by the piston after fully pressing down on the piston, or only a substantially small volume of fluid may be left between the cannula opening and the syringe.

The invention claimed is:

1. A needle hub and syringe arrangement, comprising a needle hub and a syringe, the syringe comprising a barrel and a piston, wherein:
   the needle hub comprises an axially oriented cannula bore comprising a cannula opening, wherein the cannula opening is surrounded by a substantially flat abutment plane;
   the barrel comprises an axially elongated hollow cylinder;
   the barrel is arranged as a male part configured to be received by the needle hub as a female part;
   the piston comprises at a proximal end an end-plane shaped complementary to at least part of the abutment plane, and the piston is arranged to be translated axially within the barrel between a first position and a second position, wherein
   in the first position, a volume arranged for holding a fluid is defined by part of an inner wall of the barrel, the end-plane of the piston, and at least part of the abutment plane; and
   in the second position, the end-plane of the piston abuts the abutment plane; and
   wherein the end-plane of the piston and the abutment plane are substantially planar and parallel.

2. Arrangement according to claim 1, wherein, when the piston is in the second position, the end-plane of the piston, the abutment plane and the cannula opening are substantially parallel and aligned.

3. Arrangement according to claim 1, wherein in the second position, the volume constrained between the end-plane of the piston, the abutment plane and the part of the inner wall of the barrel is smaller than 0.005 mL.

4. Arrangement according to claim 1, wherein the abutment plane comprised by the needle hub is oriented substantially perpendicular to the axial direction.

5. Arrangement according to claim 1, wherein the male part is press-fitted into the female part.

6. Arrangement according to claim 1, wherein the barrel comprises an outer wall provided with a threaded section, and the needle hub comprises at an outer wall provided with a protrusion complementary to the threaded section, arranged to be screwed into the threaded section of the barrel.

7. Arrangement according to claim 6, wherein the inner wall of the cavity of the needle hub comprises one or more recesses wherein at the one or more recesses the outer wall of the barrel when the barrel is inserted into the cavity does not touch the inner wall of the cavity.

8. Arrangement according to claim 6, wherein a first of the outer wall of the barrel and the inner wall of the cavity comprises a protruding section and a second of the outer wall of the barrel and the inner wall of the cavity comprises a receding section corresponding to the protruding section such that when the barrel is inserted into the cavity the protruding section may engage with the receding section forming a locking engagement.

9. Arrangement according to claim 8, wherein the protruding section and the receding section are provided circumferentially.

10. Arrangement according to claim 1, wherein the needle hub is arranged as the female part and the needle hub comprises a cavity for receiving at least part of the barrel arranged as the male part such that part of an outer wall of the barrel may be press-fitted against at least part of an inner wall of the cavity of the needle hub.

11. Arrangement according to claim 1, wherein the needle hub does not extend into the syringe.

12. Arrangement according to claim 1, wherein a stiffness of the first of the cavity of the needle hub and the barrel is lower than a stiffness of a second of the cavity of the needle hub and the barrel such that when the male part is inserted into the female part, the first of the cavity of the needle hub and the barrel elastically deforms according to the shape of the second of the cavity of the needle hub and the barrel.

13. Arrangement according to claim 1, wherein, when the piston is in the second position, at least 50% of the surface area of the piston end-plane contacts the abutment plane.

14. A needle hub, comprising:
a cavity arranged for receiving a syringe comprising a barrel and a piston, wherein the piston comprises, at a proximal end an end-plane, and is arranged to be translated axially within the barrel between a first position and a second position;
an axially oriented cannula bore comprising a cannula opening; and
a skirt part surrounding the cavity, wherein the cannula opening does not extend into the cavity surrounded by the skirt part; wherein
   the cannula opening is in fluid connection with the cavity;
   the cannula opening is surrounded by a substantially flat abutment plane; and
   the abutment plane is oriented perpendicular to the axial direction, wherein when the piston is in the second position, the end-plane of the piston abuts the abutment plane and the end-plane and the abutment plane are substantially planar and parallel.

15. A syringe, comprising:
a barrel, comprising an axially elongated hollow cylinder, arranged as a male part configured to be received by a cavity of a needle hub as a female part, the needle hub comprising an axially oriented cannula bore with a cannula opening surrounded by a substantially flat abutment plane; and
an axially elongated piston, arranged to be translated axially within the barrel;
wherein the piston comprises a substantially flat end-plane oriented perpendicular to the axial direction and wherein the end-plane of the piston is configured to abut the abutment plane such that the end-plane and the abutment plane are substantially planar and parallel.

* * * * *